US010253299B2

(12) United States Patent
Villain et al.

(10) Patent No.: US 10,253,299 B2
(45) Date of Patent: Apr. 9, 2019

(54) SULFATED CELLULOSE HYDRATE MEMBRANE, METHOD FOR PRODUCING SAME, AND USE OF THE MEMBRANE AS AN ADSORPTION MEMBRANE FOR A VIRUS PURIFICATION PROCESS

(71) Applicant: Sartorius Stedim Biotech GmbH, Göttingen (DE)

(72) Inventors: Louis Villain, Hannover (DE); Hans-Heinrich Hörl, Bovenden (DE); Christian Brumm, Witzenhausen (DE)

(73) Assignee: Sartorius Stedium Biotech GMBH, Goettingen (DE)

( * ) Notice: Subject to any disclaimer, the term of this patent is extended or adjusted under 35 U.S.C. 154(b) by 180 days.

(21) Appl. No.: 15/029,203

(22) PCT Filed: Sep. 11, 2014

(86) PCT No.: PCT/EP2014/002463
§ 371 (c)(1),
(2) Date: Apr. 13, 2016

(87) PCT Pub. No.: WO2015/055269
PCT Pub. Date: Apr. 23, 2015

(65) Prior Publication Data
US 2016/0257941 A1 Sep. 8, 2016

(30) Foreign Application Priority Data
Oct. 14, 2013 (DE) .......................... 10 2013 017 014

(51) Int. Cl.
*C12N 7/00* (2006.01)
*B01D 67/00* (2006.01)
(Continued)

(52) U.S. Cl.
CPC .......... *C12N 7/00* (2013.01); *B01D 67/0093* (2013.01); *B01D 69/02* (2013.01); *B01D 71/20* (2013.01);
(Continued)

(58) Field of Classification Search
CPC ............ C12N 7/00; C12N 2760/16051; C12N 2760/16151; B01D 67/0093; B01D 71/20;
(Continued)

(56) References Cited

U.S. PATENT DOCUMENTS 4,064,342 A 12/1977 Saika et al.
5,667,684 A 9/1997 Motomura et al.
(Continued)

FOREIGN PATENT DOCUMENTS

DE 3447625 7/1985
DE 102011012569 8/2012
(Continued)

OTHER PUBLICATIONS

Kobunshi Ronbunshu, Apr. 2009, vol. 66, No. 4, pp. 130-135 (English Abstract).
(Continued)

*Primary Examiner* — Pamela H Weiss
(74) *Attorney, Agent, or Firm* — McDonnell Boehnen Hulbert & Berghoff LLP

(57) ABSTRACT

The present invention relates to a sulfated cellulose hydrate membrane, a method for the preparation thereof and the use of the membrane as adsorption membrane for the purification of viruses.

14 Claims, 3 Drawing Sheets

(51) Int. Cl.
    *B01D 71/20* (2006.01)
    *B01D 69/02* (2006.01)
(52) U.S. Cl.
    CPC ...... *B01D 2323/30* (2013.01); *B01D 2325/12* (2013.01); *B01D 2325/24* (2013.01); *C12N 2760/16051* (2013.01); *C12N 2760/16151* (2013.01)
(58) Field of Classification Search
    CPC ................ B01D 69/02; B01D 2325/12; B01D 2323/30; B01D 2325/24
    See application file for complete search history.

(56) References Cited

U.S. PATENT DOCUMENTS

| | | | | |
|---|---|---|---|---|
| 5,739,316 | A * | 4/1998 | Beer | B01D 71/10 435/18 |
| 8,173,021 | B2 * | 5/2012 | Wolff | A61K 39/145 210/500.29 |
| 8,496,123 | B2 * | 7/2013 | Axen | B01D 67/0093 210/500.1 |
| 2008/0179248 | A1 * | 7/2008 | Axen | B01D 67/0093 210/650 |
| 2010/0059440 | A1 * | 3/2010 | Rudstedt | B01D 67/0093 210/651 |
| 2010/0093059 | A1 | 4/2010 | Wolff et al. | |
| 2010/0119552 | A1 * | 5/2010 | Hansen | C12N 7/00 424/232.1 |
| 2011/0147292 | A1 * | 6/2011 | Demmer | B01D 67/0093 210/198.2 |
| 2011/0163029 | A1 | 7/2011 | Faber et al. | |
| 2011/0306114 | A1 * | 12/2011 | Post Hansen | C12N 7/00 435/239 |
| 2012/0171750 | A1 | 7/2012 | Post Hansen et al. | |

FOREIGN PATENT DOCUMENTS

| | | |
|---|---|---|
| EP | 0 053 473 | 6/1982 |
| EP | 0 171 086 | 2/1986 |
| EP | 0 171 765 | 2/1986 |
| EP | 0 171 771 | 2/1986 |
| EP | 0 173 268 | 3/1986 |
| EP | 1 698 641 | 9/2006 |
| EP | 1 982 727 | 10/2008 |
| WO | WO 2008/039136 | 4/2008 |

OTHER PUBLICATIONS

Opitz et al., "Sulfated Membrane Adsorbers for Economic Pseudo-Affinity Capture of Influenza Virus Particles", Biotechnology and Bioengineering, vol. 103, No. 6, pp. 1144-1154, Aug. 15, 2009.

Wolff et al., "Purification of Cell Culture-Derived Modified Vaccinia Ankara Virus by Pseudo-Affinity Membrane Adsorbers and Hydrophobic Interaction Chromatography", Biotechnology and Bioengineering, vol. 107, No. 2, pp. 312-320, Oct. 1, 2010.

Raiado-Pereira et al., "Grafting Hydrophobic and Affinity Interaction Ligands on Membrane Adsorbers: A close-up "view" by X-ray Photoelectron Spectroscopy", Separation and Purification Technology, vol. 93, pp. 75-82, Mar. 22, 2012.

English translation of Notice of Reasons for Rejection issued by the Japanese Patent Office in application No. 2016-522736, dated May 10, 2017.

* cited by examiner

—△— Sulfated membrane according to example 4
—□— Cellufine® Sulfate from JNC
—●— Capto® DeVirS from GE Healthcare

SULFATED CELLULOSE HYDRATE MEMBRANE, METHOD FOR PRODUCING SAME, AND USE OF THE MEMBRANE AS AN ADSORPTION MEMBRANE FOR A VIRUS PURIFICATION PROCESS

FIELD OF THE INVENTION

The present invention relates to a sulfated cellulose hydrate membrane, a method for the preparation thereof and the use of the membrane as adsorption membrane for the purification of viruses.

BACKGROUND OF THE INVENTION

Influenza (influenza virus) is a highly infectious acute infection of the upper and lower respiratory tracts, which is triggered by influenza viruses. Influenza occurs as a worldwide epidemic, particularly in the winter months, although individual viruses can also trigger pandemics. Current strategies to control influenza outbreaks are based on prophylactic vaccinations in combination with antiviral treatments, for example, with neuraminidase inhibitors. A majority of seasonal human influenza vaccines are inactivated trivalent split virion vaccines. These are composed of viral antigens, the envelope glycoprotein hemagglutinin (HA) and neuraminidases (NA) of three different influenza virus sub-types. The respective antigens are obtained from purified virus particles by membrane solubilization using detergents (e.g. CTAB (cetyltrimethylammonium bromide) or Tween 20 (polysorbate 20)).

In classical production processes, the influenza viruses are produced in incubated chicken eggs. In addition to the limited scalability of this process and the problems linked thereto, there are systemic difficulties in producing individual pandemic influenza viruses (e.g. H5N1) in chicken eggs to meet the growing demand of the worldwide market. Lastly, the issue of allergic reaction to chicken protein has also meant that production processes using mammalian cells in bioreactors have been established for several years. After culturing viruses in cell cultures it is necessary to separate the viruses from the contaminants (e.g. host cell proteins, DNA) so that they can be further used in their pure form. It is advantageous, furthermore, to separate infectious from non-infectious molecules or particles. In biopharmaceutical production processes, deoxyribonucleic acid (DNA), and other proteins arising from the host cell culture, occur as by-products. These generally count as contaminants and must be removed from the end product during the work-up. In the production of viruses, DNA fragments of the host cells or of the viruses themselves are also released which have to be removed.

The adsorption of viruses on solid phases by chromatographic purification has a major significance in virus purification, especially on a process scale. This is characterized in that molecules are bound to the adsorber material (ion exchanger, hydrophobic or hydrophilic adsorbents) and may then be eluted in a purified form in a subsequent step. In this case, it is important that the adsorption process proceeds reversibly so that high yields are achieved. Either a simple enrichment or a separation into two or more target substances can be carried out where, in the latter case, either the adsorption or the desorption or both can be effected selectively. The major disadvantage of the chromatographic media used for this purpose is their relatively low selectivity, and the contaminants (DNA fragments and host cell proteins) present in solution can also bind to the adsorber material such that long process development times are required in order to determine the optimal binding and elution conditions (pH, ionic strength and selection of the buffer systems).

Affinity chromatography offers enhanced selectivity. It is known from the prior art that sulfated cellulose matrices have enhanced selectivity towards influenza viruses and heparin-binding proteins.

EP 0 053 473 A1 discloses cellulose sulfate salts having heparin-like effect for use as anticoagulants. For sufficiently high anti-coagulant effect, together with desired high long-term stability under physiological conditions, the degree of sulfation (the degree of substitution of the OH groups by sulfate groups on the C2, C3 and C6 atom of the glycopyranose units) of the cellulose is between 0.8 and 2.6. The cellulose sulfate salts are obtainable by three different methods: by reaction with chlorosulfuric acid in the presence of an amine, by reaction with $SO_3$-amide complexes in which, for example, dimethylformamide may be used as amide, or by reaction with $SO_3$-amine complexes in which, for example, pyridine may be used as amine. In the latter variant mentioned, the cellulose is reacted with an $SO_3$-pyridine complex at room temperature for 30 to 35 minutes and subsequently neutralized with NaOH.

EP 1 698 641 A1 discloses cellulose sulfate salts as therapeutic active ingredients for skin disorders such as atopic eczema. The cellulose sulfate salts are characterized by an inhibitory effect on hyaluronidase and have a sulfate content of 6.5 to 19.0% by weight based on the total weight of the cellulose sulfate salt. In the preparation, crystalline cellulose is firstly pre-swollen in a solvent such as pyridine, dimethyl sulfoxide or dimethylformamide. The resulting mixture is added to a sulfating reagent selected from the group of chlorosulfonic acid, piperidine-sulfuric acid complex, $SO_3$-pyridine complex, $SO_3$-trimethylamine complex or sulfuric acid anhydride-dimethylformamide complex, wherein the latter mentioned complex is preferred.

Both documents mentioned above, EP 0 053 473 A1 and EP 1 698 641 A1, do not disclose any chromatographic separating materials for purifying viruses. Such separating materials are commercially available as gels and are used for the purification of the molecules and viruses mentioned above. Use of these media for purifying viruses often affords low binding capacities for the viruses and low virus yields. Viruses may have sizes up to 500 nm and particulate chromatography gels with pore sizes in the range of 30 to 400 nm are therefore not very suitable. Typically, viruses can then only bind to the outer surface of the particle which explains the low binding capacities.

The sulfating of chromatographic gels composed of cellulose, dextran or agarose and the use of these sulfated gels for purifying influenza viruses are known from the prior art. By way of example, RD 298 025 A discloses affinity chromatography gels which can be prepared by sulfating "Cellulofine GH-25", "Sepharose CL-6B" or "Sephadex G-50" with a chlorosulfonic acid-pyridine complex at 65 to 70° C., subsequent neutralization with NaOH and washing with phosphate-buffered saline solution. The gels are suitable for purifying proteins such as hepatitis B antigens, HIV-1 and HIV-3 viruses, SV40-T antigens, blood-clotting factors 7, 8, 9 and 11, nucleic acid polymerases, interferones or lysozyme.

EP 0 171 086 A2 describes a method for sulfating (partially) crystalline polysaccharide gels based on agarose, dextran or cellulose with chlorosulfonic acid or anhydrous sulfuric acid in pyridine at 65 to 70° C. The degree of sulfation of the polysaccharide gels is generally between 0.1 and 40%, whereas the degree of sulfation of the cellulose gels is specifically between 0.1 and 5%. Influenza viruses or antigens from chicken embryo cell cultures can be purified with the sulfated cellulose gels.

WO 2008/039136 A1 discloses a porous polysaccharide matrix, preferably from agarose, to which "extender" molecules of 500 kDa dextran are bound, wherein sulfate groups are in turn bound to the dextran molecules as ligands, for purifying viruses. The matrix is used for the separation of viruses, preferably influenza viruses, from DNA contaminants, in which the viruses are initially adsorbed on the matrix and are subsequently eluted with a suitable buffer. To prepare the aforementioned matrices, sulfate ligands are firstly bound to the "extender" molecules before the sulfated "extender" molecules are fixed on the polysaccharide matrix.

EP 0 171 771 A2 discloses the use of the sulfated cellulose gels known from EP 0 171 086 A2 for purifying rabies viruses from chicken embryo cell cultures.

EP 0 173 268 A2 discloses the use of the sulfated cellulose gels known from EP 0 171 086 A2 for purifying glycoproteins gA and gB as constituents of herpes simplex viruses of the HSV-1 and HSV-2 types, which are obtained from lysates of mammalian cell cultures. The glycoproteins gA and gB are purified in the presence of an anionic or non-ionic surfactant.

EP 0 171 765 A2 discloses a method for purifying Japanese encephalitis virus for vaccine production, in which the sulfated cellulose gels known from EP 0 171 086 A2 are used.

All aforementioned documents disclose chromatographic separation media consisting of particulate porous gel particles. For this purpose, polysaccharide gels having a molecular weight cut-off (MWCO) of less than $10^7$ Da are used as base material for the sulfation reaction. Viruses, such as e.g. influenza viruses having a diameter greater than 100 nm and a molecular mass (MW) greater than $10^8$ Da, as described by R. W. H. Ruigrok et al. in J. Gen. Virol. (1984), 65, 799-802, can only penetrate to a limited extent the pores of the porous separation materials described, in which case only a part of the binding capacity of these separation materials can be exploited.

Adsorption membranes, in contrast to particulate adsorbents, have substantially larger pores which are fully accessible to viruses. In addition, they offer the possibility to force perfusion with the medium, by applying a hydraulic pressure difference between their two main surfaces, whereby instead of a purely diffusive transport of the adsorbents in the direction of a concentration gradient into the adsorbent interior, a convective transport is achieved which can be effected much more rapidly at high flow. A further inherent disadvantage of particulate adsorbents can thereby be avoided, which is referred to as "diffusion limiting", which consists of the fact that, with increasing particle size of the adsorbent and increasing molar mass of the adsorbent, the time required for establishing the adsorption equilibrium increases considerably, which translates into deterioration of the kinetics. For this reason, only low flow rates are typically achieved with chromatographic gels in the purification of influenza viruses for example.

Sulfated membrane adsorbers based on cellulose have already been successfully produced by sulfating a cellulose hydrate membrane, in which the sulfation is typically effected by reaction of the cellulose membrane with a Lewis base-$SO_3$ complex in a solvent suitable for the reaction. Compared to conventional sulfated polysaccharide gels, sulfated membrane adsorbers have the following advantages:
- convective flow in contrast to diffusive "flow" in particulate separating materials
- higher flow rates possible
- better accessibility to the ligands and higher binding capacity for viruses
- simpler scalability, i.e. increasing scale from low-volume membrane adsorbers to large-volume membrane adsorbers.

Since the capacity is a function of the ligand density and the available binding surface, this is typically increased by decreasing the membrane pore size, which can, however, have a negative effect in respect of the flow and blocking up characteristics.

U.S. Pat. No. 5,667,684 discloses microporous membranes for removing HIV viruses from blood plasma, which consist of a hydrophobic base material, e.g. polypropylene, polyethylene or polyvinylidene fluoride, onto which a chain of alkoxyalkyl acrylates, glycidyl acrylates or acrylamides have been grafted.

Sulfated cellulose is immobilized on this intermediate graft layer by covalent binding, in which, for example, free OH groups of the sulfated cellulose are reacted with functional groups, epoxide groups for example, of the repeating units of the graft chain. The HIV viruses are predominantly removed by the sulfated cellulose units.

U.S. Pat. No. 8,173,021 B2 discloses a preparation process for sulfated, non-crosslinked cellulose membranes having a degree of sulfation (sulfony group content) between 0.5 and 15%, in which cellulose membranes are reacted with a chlorosulfonic acid-pyridine complex at not more than 40° C. The chlorosulfonic acid-pyridine complex is prepared by adding chlorosulfonic acid to pyridine at a maximum of 0° C., subsequent reaction at 60° C. and cooling to a maximum of 40° C. The sulfated cellulose membranes, which can be prepared from non-crosslinked, regenerated cellulose membranes (e.g. RC-55 membranes from Whatman), are used in affinity chromatography for purifying protein-containing virus fragments or for purifying intact virus particles, which are used subsequently in influenza vaccine production.

L. Opitz et al., Biotechnology and Bioengineering, 103 (6), 2009, 1144-1154, disclose the preparation of sulfated cellulose membranes by reacting strengthened, non-crosslinked cellulose membranes with a solution of chlorosulfonic acid in pyridine at 37° C. for 12 hours. The sulfur content of the sulfated cellulose membranes, at 16 µg of sulfur/g of dried membrane, is significantly lower than in the particulate adsorbent Cellufine® Sulfate (≥700 µg of sulfur/g of dried membrane). The sulfated cellulose membranes are used for purifying three influenza strains, i.e. H1N1, H3N2 and "B/Malaysia/2506/2004" viruses, in which undesired contaminants, such as double-stranded DNA or cell constituents, are effectively removed from the cell culture solution used for the production of the viruses. With increasing NaCl concentration in the buffer solution used for the purification (150 nM versus 50 mM), the adsorption capacity of the membranes for the viruses decreases. In comparison to cation exchanger membranes, such as Sartobind® S75 or Sartobind® C75, the sulfated cellulose membranes allow an improved depletion of double-stranded DNA and permit a higher virus yield than chromatography columns based on Cellufine® Sulfate.

US 2012/0171750 A1 investigates the influence of reaction temperature on the degree of sulfation of the cellulose matrix in the preparation of sulfated cellulose matrices known from the aforementioned article by L. Opitz et al., the adsorption capacity for MVA viruses and the contamination of the purified MVA virus preparation with DNA from the cell culture solution. With increasing reaction temperature in the sulfation (35, 40 or 45° C.), the degree of sulfation of the cellulose matrix increases from 5.3 to 13% by weight, based on the weight of the cellulose polymer backbone, while the DNA fraction in the purified virus preparation increases from 7.4% to 17% and the yield of purified MVA viruses increases from 66 to 80%. The purification of the virus preparation by means of sulfated cellulose matrices may be combined with an additional step of hydrophobic interaction chromatography, in which chromatography matrices having phenyl, butyl or hexyl ligands are used.

Using the method known from U.S. Pat. No. 8,173,021 B2, a degree of sulfation greater than 15% cannot be achieved despite using relatively fine membranes (RC-55 membranes from Whatman with a pore size of 0.45 μm). The selected pore size is also unfavourable for binding viruses having a diameter of more than 100 nm, since loss of flow and blocking up of the membrane during the adsorption of the viruses can occur.

SUMMARY OF THE INVENTION

The object of the present invention, therefore, is to provide membranes for the purification of viruses, influenza virus purification for example, which on the one hand have a high selectivity for the target compounds to be isolated, and on the other hand enable an effective removal of undesired contaminants, such as double-stranded DNA or cell constituents, from the cell culture solution used for the production of viruses, at high flow rates.

This object is achieved by the subject matter characterized in the claims.

In particular, the present invention provides a sulfated cellulose hydrate membrane comprising a crosslinked cellulose hydrate matrix with pores which extend from one main surface to another main surface of the membrane, wherein the cellulose hydrate membrane has sulfate ligands on its inner and outer surfaces for the adsorptive substance separation.

In accordance with the present invention, the sulfated cellulose hydrate membrane is an adsorption membrane. The adsorption membranes referred to are sheetlike adsorbents with pores passing through from one side to the other side. Adsorbents are porous solids which can accept selective binding with particular components of fluids via surface functional groups referred to as ligands. Target substance(s) and/or contaminant(s) are referred to as adsorbates in accordance with the invention, which can also take the form of two or more different substances. Adsorbates can be individual molecules, associates or particles which, in the case of target substance(s), are preferably viruses.

In accordance with the present invention, the crosslinking of the cellulose hydrate matrix is effected prior to it being sulfated in a subsequent process step. It has been found, surprisingly, that the prior crosslinking of the cellulose hydrate membrane to be sulfated leads to an increased permeability for reverse osmosis water (RO water), to an increased sulfate ligand density, to an enhanced binding capacity and to an enhanced binding selectivity for the target compounds to be isolated, particularly for influenza viruses, wherein these advantageous effects cannot be achieved by using sulfated cellulose membranes which have not been crosslinked prior to their sulfation. In contrast to U.S. Pat. No. 8,173,021 B2 and US 2012/0171750 A1, significantly higher sulfate ligand densities can be achieved, surprisingly, by the sulfation of a crosslinked cellulose membrane than are achievable by the prior art.

The sulfate ligand density according to the invention is determined by the degree of sulfation in which, in accordance with a preferred embodiment of the sulfated cellulose hydrate membrane according to the invention, the degree of sulfation of the cellulose hydrate matrix is 10% by weight or more, more preferably 15% by weight or more, and particularly preferably more than 20% by weight, which leads to an improved selectivity in favor of virus production. In accordance with the invention, the degree of sulfation is understood to mean the proportion by mass of sulfate groups on the sulfated cellulose hydrate matrix. The degree of sulfation is determined quantitatively by titration, in which the quantitative amount of sulfate groups on the membrane can be determined, for example, using aqueous sodium hydroxide solution.

The degree of sulfation is determined according to the present invention using the formula below:

$$\text{Degree of sulfation in \% by weight} = (n_{sulfate} \times M(SO_3))/(m_{cellulose} + (n_{sulfate} \times M(SO_3))) \times 100\%$$

where $m_{cellulose}$ = mass of cellulose in μg per cm² of membrane and the sulfate group density $n_{sulfate}$ which is determined by means of the following formula:

$$\text{Sulfate group density: } n_{sulfate} \, (\mu mol/cm^2) = c(NaOH) \times t(NaOH) \times V(NaOH) \times 1000/A$$

where c(NaOH) quantitative concentration of aqueous sodium hydroxide titrant in mol/l
V(NaOH) volume in ml of titrant consumed at the equivalence point (pH 7)
t(NaOH) correction factor of titrant
1000 conversion factor from mol/l to μmol/ml
A active filter surface in cm²
and where
$M(SO_3)$ molar mass of $SO_3$ in μgμmol.

In comparison with sulfation of non-crosslinked cellulose membranes, the sulfate ligand density can be increased, surprisingly, by a factor of up to 30 by the crosslinking of the cellulose membranes in accordance with the present invention, compared with the comparative examples from the prior art (samples 1 and 3 in table 2). This is even possible with cellulose membranes having a mean pore size of more than 0.45 μm.

An additional surprising consequence of the prior crosslinking of the cellulose hydrate membranes is the increase in permeability linked thereto and the decrease in the binding capacity for small proteins or contaminants, such as host cell proteins, despite increasing sulfate ligand density, which results in an improved selectivity favorable to virus production.

As is described below, the method for preparing the membrane according to the invention may be carried out in two steps: crosslinking the membrane and sulfating the membrane.

The degree of crosslinking, the pore size and, as a consequence, the permeability of the membrane and the accessibility of the hydroxyl groups for the further sulfation reaction may be controlled by the type of crosslinker, the concentration of the crosslinker, the concentration of a crosslinking catalyst optionally used, the crosslinking duration, if appropriate, the type and the concentration of an inert organic solvent and/or the crosslinking temperature.

In accordance with a preferred embodiment of the sulfated cellulose hydrate membrane according to the invention, the degree of crosslinking is between 0.05 and 0.5, in which the mean degree of substitution of the anhydroglucose units of the cellulose by reaction with the difunctional crosslinker is selected as a measure for the degree of crosslinking (DC). In this case, the degree of crosslinking according to the invention, as described in WO 95/32793 A1, is defined as:

$$DC = 3.24 \Delta \Delta M / M_Y$$

where

DC: degree of crosslinking of the membrane according to the invention

ΔM: mass increase of the membrane according to the invention by the crosslinking in % of the initial mass of the starting membrane, $M_Y$: molar mass of the crosslinker Starting from a difunctional crosslinker and assuming that each of these binds to two cellulose monomer units, then at most three crosslinker molecules can react with two cellulose monomer units. These have a combined molar mass of 324 g/mol. The theoretical maximum possible value of DC is at most 3, due to the three crosslinkable hydroxyl groups of the cellulose monomer unit.

According to the present invention, the sulfated cellulose hydrate membrane is suitable for adsorptive substance separation, particularly for the efficient purification of viruses. This is possible, in particular, if the molecular weight cut-off of the sulfated cellulose hydrate membrane according to the invention is selected such that the target substances do not block the membrane surface, whereby a high flow rate can be maintained. Depending on the desired target substance, the molecular weight cut-off can be set such that the target substance is adsorbed within the sulfated cellulose hydrate membrane and can be subsequently eluted therefrom. The mean pore size of the membrane according to the invention is preferably between 0.5 and 5.0 μm and particularly preferably between 1.0 and 3.0 μm.

Starting Membrane:

The cellulose hydrate membrane used as starting membrane in the method according to the invention with a mean pore size of 0.1 to 20 μm, preferably 0.5 to 15 μm, and more preferably 1 to 10 μm, is prepared by a customary preparation method known from the technical field such as is described, for example, in L. J. Zeman et al., "Microfiltration and ultrafiltration principles and applications", Marcel Dekker 1996, "Part I", "Chapter 3.1", DE 103 26 741 A1 and DE 34 47 625 A1. To determine the mean pore size, a "capillary flow porometry test" was carried out. Details can be found in the operating instructions for the "Capillary Flow Porometer 6.0", CAPWIN Software System, Porous Materials Inc.

It is preferable in accordance with the present invention that cellulose ester membranes, which have been optionally subjected to a pretreatment described below, are saponified with a suitable saponification medium, in which case the cellulose hydrate membrane is formed. Depending on the type of pretreatment medium, the cellulose ester membrane can be used dry or wet in the saponification step.

Cellulose ester membranes can be based on cellulose monoacetate, cellulose diacetate, cellulose triacetate, cellulose propionate, cellulose butyrate and cellulose acetobutyrate or other suitable cellulose esters or cellulose nitrate, methylcellulose or ethylcellulose or mixtures thereof, where cellulose acetate(s) (is) are preferred, particularly cellulose diacetate. The cellulose ester membrane in this case can be pretreated in a suitable medium before the saponification step, where the pretreatment medium comprises one or more additive(s) which has/have a dissolving or softening effect on a cellulose ester. Suitable additives are especially acids, particularly carboxylic acids such as acetic acid, and water-soluble softeners for cellulose esters such as diacetin, triacetin and sulfolane.

The saponification medium preferably comprises an alkaline compound, preferably an alkali metal hydroxide. Particular preference is given to using an aqueous solution of sodium, potassium or lithium hydroxide. It is also possible to use mixtures of an alkali metal hydroxide and other alkaline compounds such as alkali metal carbonate, such as sodium carbonate, potassium carbonate, cesium carbonate, sodium hydrogen carbonate and/or sodium triphosphate, potassium triphosphate, sodium silicate and potassium silicate.

The resulting cellulose hydrate membrane can have any suitable thickness. The membrane thickness is preferably in the range between 50 and 500 μm, more preferably in the range between 100 and 300 μm. The cellulose hydrate membrane obtained can be formed as a sheetlike membrane or cylindrically. Cylindrical membranes are referred to as hollow fiber membranes, capillary membranes or tubular membranes.

Crosslinking:

The crosslinker has at least two functional groups in the molecule which react with the hydroxyl groups of the cellulose membrane and thus enable crosslinking of the cellulose membrane. For example, the crosslinking of the cellulose membrane is effected via the (intermolecular) linking of two cellulose polymer chains or via the (intramolecular) linking of repeating units of a cellulose polymer chain by the aforementioned crosslinker having at least two functional groups which are reactive towards hydroxyl groups of the cellulose polymer chains. The crosslinkers which can be used are not in principle subject to any particular limitations and a person skilled in the art is able to select them with regard to the reaction conditions of the subsequent sulfation. However, in the crosslinking step, preference is given to using a diepoxide compound or also other compounds having at least two reactive functional groups reactive with hydroxyl groups of cellulose, such as diisocyanate, epichlorohydrin, epibromohydrin, dimethylurea, dimethylethyleneurea, dimethylchlorosilane, bis(2-hydroxyethylsulfone), divinylsulfone, alkylene dihalides, hydroxyalkylene dihalides and diglycidyl ethers. Particular preference is given to using a diepoxide compound in the crosslinking step.

From the group of diglycidyl ethers, preference is given to 1,4-butanediol diglycidyl ether, ethylene glycol diglycidyl ether, glycerol diglycidyl ether and polyethylene glycol diglycidyl ether.

Particular preference is given to the use of 1,4-butanediol diglycidyl ether or ethylene glycol diglycidyl ether as crosslinker.

Optionally, a mixture of different crosslinkers may be used.

The crosslinking can take place in an aqueous medium, in an organic solvent or also in a mixture of water and an organic solvent. The crosslinking is preferably carried out in an aqueous medium.

Preference is also given to using a crosslinking catalyst, such as sodium hydroxide or potassium hydroxide, to accelerate the crosslinking of cellulose with the crosslinker.

The temperature of the medium used in the crosslinking step can be from about 4° C. up to the boiling point of the crosslinking medium, wherein a temperature in a range from 5° C. to about 85° C. is preferred. Particular preference is given to a temperature of 20° C. to 40° C.

The crosslinking duration is typically a few minutes up to several days, wherein a crosslinking duration of 12 hours to 7 days at 15 to 30° C. is preferred. Particular preference is given to a crosslinking duration of 1 to 3 days. In a preferred embodiment of the method according to the invention for preparing the membrane according to the invention, the concentration of the crosslinker in the crosslinking solution is between 10 and 30% by weight.

As described above, the degree of crosslinking of the sulfated cellulose hydrate membrane according to the invention is at least 0.05, more preferably at least 0.07 and particularly preferably at least 0.1. The upper threshold of the degree of crosslinking is preferably 0.5, more preferably 0.4 and particularly preferably 0.3.

Further advantageously, the membranes according to the invention have a higher chemical stability due to the crosslinking and can therefore tolerate higher reaction temperatures (up to 90° C.) during the subsequent sulfation process.

Sulfation:

The sulfation is effected by reacting the crosslinked cellulose hydrate membrane with a Lewis base-$SO_3$ complex. The reaction can be effected with chlorosulfuric acid in the presence of an amine or by reaction with $SO_3$-amide complexes, wherein dimethylformamide can preferably be used as amide, or by reaction with $SO_3$-amine complexes, wherein pyridine or trimethylamine can preferably be used as amine. The $SO_3$-pyridine complex is particularly preferred for the reaction.

The concentration of the $SO_3$-pyridine complex in the sulfation solution is typically 1 to 40% by weight, particular preference being given to concentrations between 10 and 30% by weight.

Typically, aprotic polar solvents such as dimethylformamide (DMF), dimethylsulfoxide (DMSO), dimethylacetamide (DMAc), N-methyl-2-pyrrolidone or 2-pyrrolidone for example can be used as solvent for the reaction with the $SO_3$-amine complex. Particular preference is given to 2-pyrrolidone.

The reaction duration is between 30 min to 24 hours, particular preference being given to reaction durations of between 1 and 4 hours.

The reaction temperature is between 20 to 90° C., particular preference being given to reaction temperatures of 70 to 90° C.

DESCRIPTION OF THE DRAWINGS

The present invention is illustrated in detail by means of the following working examples and FIGS. 1 to 3. These show FIG. 1 the influence of the degree of crosslinking on the degree of sulfation of the membrane according to the invention, on the permeability for RO water and on the binding capacity for lysozyme, FIG. 2 the dynamic binding capacity for influenza viruses and lysozyme, and FIG. 3 breakthrough curves of sulfated polysaccharide gels from the prior art and of an inventive sulfated cellulose membrane loaded with HCP solution ("host cell protein" solution).

DESCRIPTION OF THE INVENTION

Working Examples

Five different membranes were functionalized in order to illustrate the influence of crosslinking. Two different sulfation methods were applied both to crosslinked and non-crosslinked cellulose hydrate membranes (comparative examples) with the same pore size (samples 1 to 4).

A further sample was prepared which was crosslinked according to example 1 and sulfated according to example 2 (sample 5). This sample differs from samples 1 to 4 in that a narrower starting membrane with a mean pore size of 1.2 µm was used for the sulfation. All membrane samples were characterized according to examples 5 to 8. The results are summarized in table 2. The Sartobind® S sample is a cellulose hydrate membrane with sulfonic acid ligands.

Figure 1:
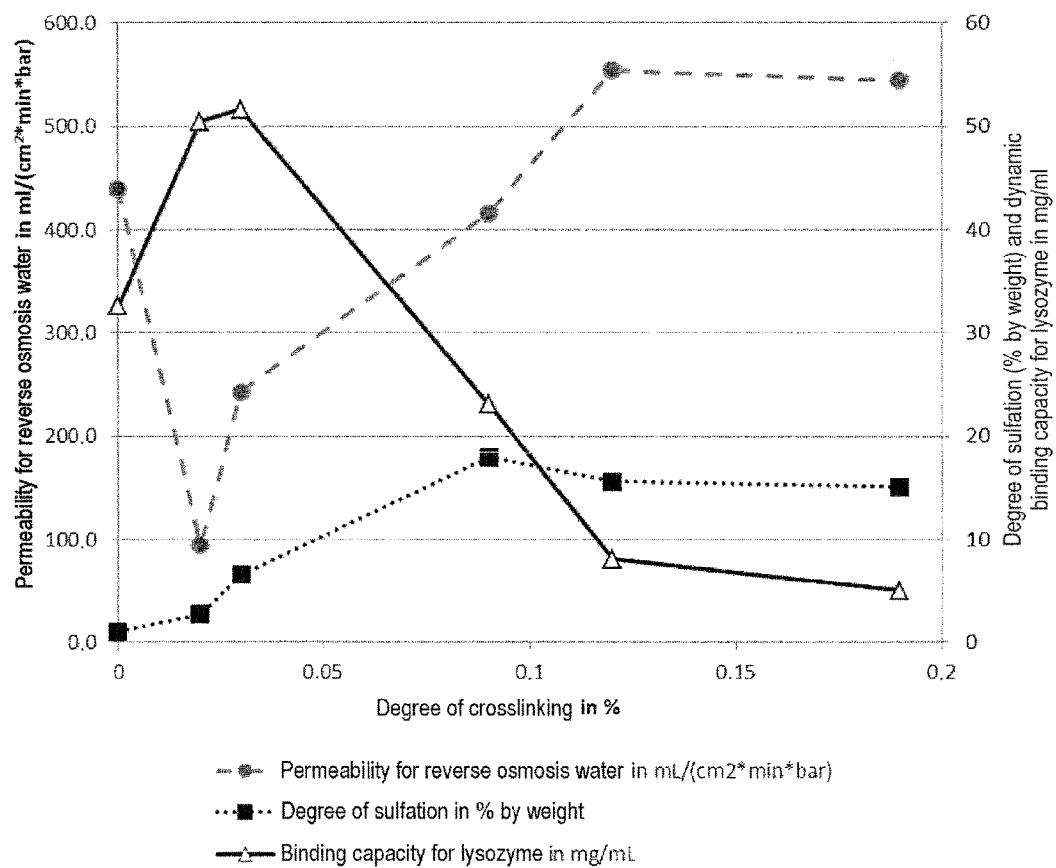

FIG. 1 shows that the increase in the degree of crosslinking leads to an increase in the degree of sulfation but also to an increase in the flow rate of RO water. In addition, the sulfated membranes crosslinked according to the invention have a higher selectivity for influenza viruses compared to contaminants, since they show experimentally a significantly lower dynamic binding capacity for small negatively charged proteins such as lysozyme. The degree of sulfation in FIG. 1 is stated in % by weight. Table 1 comprises the details of the composition of the crosslinking solutions which were used for preparing the membranes of FIG. 1.

Figure 2:
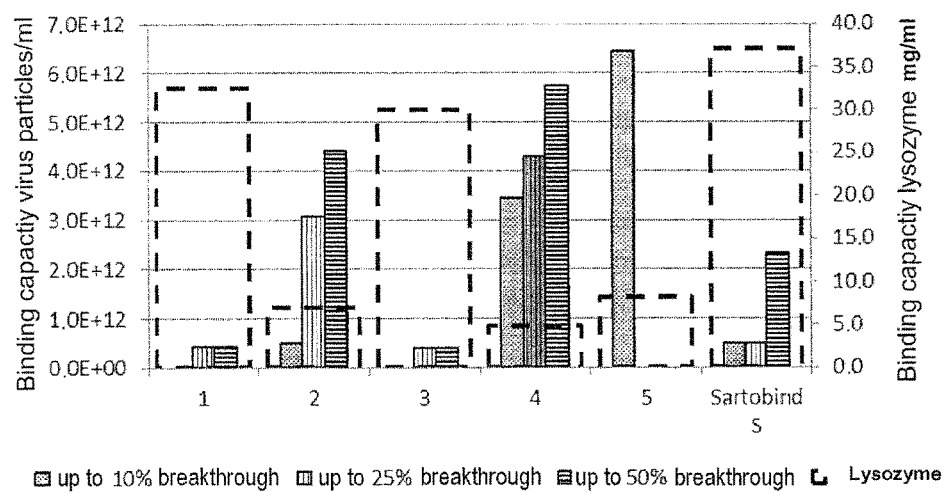

FIG. 2 shows that the membranes of samples 2, 4 and 5 according to the invention have distinctly better binding properties, since they have a higher dynamic binding capacity for influenza viruses, than the membranes of samples 1 and 3 which were selected as comparative examples. The membrane of sample 5 has a higher dynamic binding capacity for influenza viruses by at least a factor of 10, compared to samples 1 and 3. In addition, in the membranes of samples 2, 4 and 5, the binding capacity for small, positively charged protein contaminants such as lysozyme is only ⅓ of that of the non-crosslinked samples 1 and 3 and the "Sartobind® 5" membrane which has cation exchanging sulfonate groups as ligands. The membrane of sample 5 according to the invention therefore has the highest selectivity for binding of influenza viruses of all samples investigated.

The descriptor "E+12" in FIG. 2 means "$\times 10^{12}$".

Figure 3:
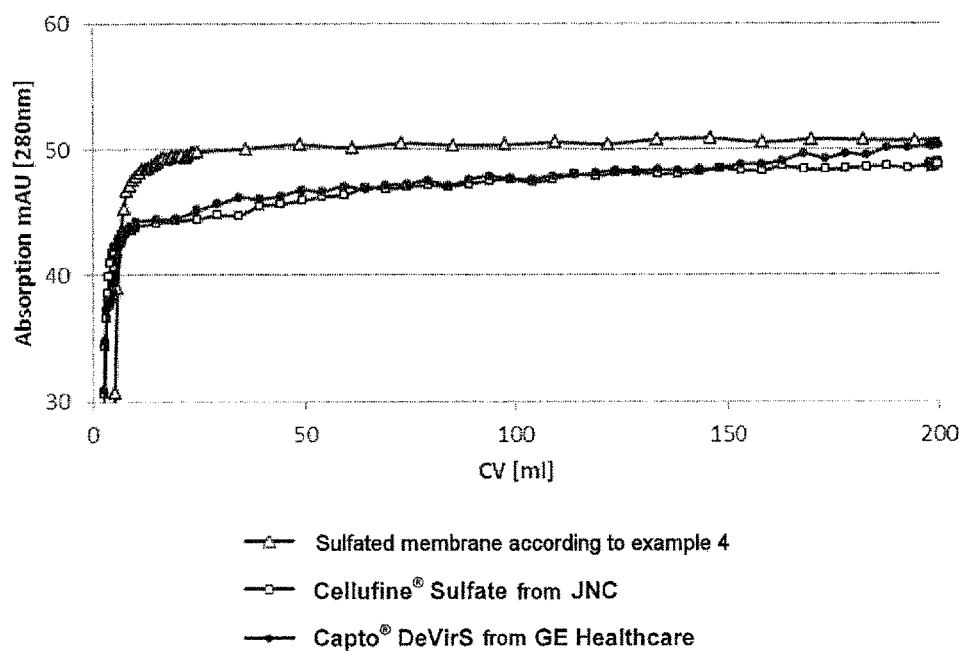

The breakthrough curves with HCP solution (host cell protein solution) presented in FIG. 3 show that the sulfated membrane of sample 4, unlike conventional sulfated polysaccharide gels, practically does not bind any contaminants such as host cell proteins (HCP). In this case, Cellufine® Sulfate from JNC Corporation and Capto® DeVirS from GE Healthcare were used for comparison. In the membrane of sample 4 according to the invention, an immediate breakthrough of host cell proteins (HCP) occurs, which proves that this membrane does not bind any HCP. In the sulfated gels regarded as comparative examples, the UV signal of the HCP solution originally used is only achieved again after 100 ml colume volume (CV [ml]=column volume in ml), which proves that the sulfated gels bind these contaminants to a considerable extent. The property of the membranes according to the invention described above is of major advantage in the purification of viruses, since contaminants such as HCP cannot bind to the membrane material and, after elution of the virus, are therefore not found in the eluate. For this reason, further contamination depletion steps can be omitted and the total costs of the purification process are significantly reduced. It is also clearly apparent here that the higher sulfate ligand density in the membrane according to the invention has no negative effect on the binding of contaminants and, in a desired manner, selectively improves only the binding capacity for influenza viruses.

Example 1: Crosslinking of Cellulose Microfilter Membranes

The crosslinking reaction takes place at 20 to 25° C. 10% aqueous sodium hydroxide solution is added to a precharged amount (in g) of reverse osmosis water and stirred. 1,4-Butanediol diglycidyl ether (Sigma-Aldrich, Cat. No.: 220892) is then added and stirred until a homogeneous solution is formed. The degree of crosslinking can be controlled by the concentration of 1,4-butanediol glycidyl ether in the crosslinking solution. The respective amounts of reverse osmosis water, aqueous sodium hydroxide solution and 1,4-butanediol diglycidyl ether (BUDGE) in the crosslinking solutions prepared here and the resulting degree of crosslinking of the membrane according to the invention are summarized in table 1.

TABLE 1

Composition of the crosslinking solutions and resulting degree of crosslinking

| 10% NaOH/ [g] | ROW/ [g] | BUDGE [g] | Degree of crosslinking |
|---|---|---|---|
| 6.0 | 94.0 | 0.0 | 0 |
| 6.0 | 93.0 | 1.0 | 0.02 |
| 6.0 | 92.0 | 2.0 | 0.03 |
| 6.0 | 89.0 | 5.0 | 0.09 |
| 6.0 | 84.0 | 10.0 | 0.12 |
| 6.0 | 79.0 | 15.0 | 0.19 |

A DIN A4 sheet of dry cellulose microfilter membrane from Sartorius Stedim Biotech GmbH (type 10142V) is completely wetted with the crosslinking solution and then stored for seven days in an airtight polyethylene bag. After completion of the crosslinking reaction, the microfilter membrane is rinsed with running reverse osmosis water for 10 min and then dried in a convection oven at 80° C. for 10 to 12 minutes.

To determine the degree of crosslinking as defined above, the following procedure is carried out: the non-crosslinked cellulose membranes of type 10142V are dried in a Sartorius moisture analyzer balance (type MA100) at 110° C. for 5 min and their weight $m_A$ is determined. Then, the membranes are wetted with the crosslinking solution. An additional blank sample, which is not treated with crosslinker, is weighed to determine the weight loss due to leachable constituents. After a crosslinking time of 7 days, the membranes are rinsed for 10 minutes with running RO water and then pre-dried in a convection oven at 80° C. for 10 min and finally—as the starting membranes—dried on the moisture analyzer balance for 5 min and $m_V$ is determined. By means of the blank sample untreated with crosslinker, the mass of leachable constituents $m_B$ is determined. The percentage increase in mass $\Delta M$, required for the value defined, arises as follows:

$$\Delta M = 100\% * ((m_V - m_A - m_B)/(m_A - m_B)),$$

where $m_V$ mass of the crosslinked membrane
$m_A$ mass of the non-crosslinked membrane and
$m_B$ mass of the leachable constituents of the blank sample.

Example 2: Sulfation with 2-Pyrrolidone and Pyridine-Sulfur Trioxide Complex 2 g of pyridine-sulfur trioxide complex (Sigma-Aldrich, Cat. No. 84737-500g) are added to 8 g of 2-pyrrolidone with stirring. The reaction vessel is tightly sealed. The mixture is then temperature controlled at 70° C., whereupon the pyridine-sulfur trioxide complex dissolves and an ochre-colored sulfation solution is formed.

Into the base of an 80 ml weighing bottle with ground glass lid heated to 70° C. are pipetted 3.8 g of freshly prepared sulfation solution heated to 70° C. Circular dry cellulose microfilter membrane discs (diameter 70 mm) of the non-crosslinked membrane (comparative example, starting membrane of example 1 of type 10142V) and the membrane crosslinked according to example 1 are placed successively in the sulfation solution; they are wetted spontaneously in this case. The reaction vessel is then immediately tightly sealed.

The reaction vessel is then stored for 4 hours at 70° C. in the convection drying cabinet. The sulfated cellulose microfilter membranes are subsequently rinsed with running reverse osmosis water for 10 min, shaken in 100 g of 1M NaCl solution for 5 min and then rinsed under running reverse osmosis water for 5 min. The membranes are then shaken in 100 g of a solution of 30% by weight glycerol and 70% by weight water for 5 min and subsequently dried at 80° C. for 10 min.

Example 3: Sulfation with Pyridine and Chlorosulfonic Acid

Pyridine (Sigma-Aldrich, Cat. No. 270970-1L) and chlorosulfonic acid (Sigma-Aldrich, Cat. No. 571024-100G) are cooled to −18° C. prior to use. With vigorous stirring, 60 ml of chlorosulfonic acid are added dropwise to 1000 ml of pyridine over 15 min via a pressure-equalizing dropping funnel and drying tube, wherein a temperature of 5° C. must not be exceeded; a white solid precipitates here.

The mixture is then tightly sealed and heated to 65° C. under stirring in a water bath until the solid has completely dissolved. The sulfation solution thus obtained is then cooled to 40° C. over one hour.

Non-crosslinked membrane strips (comparative example from example 1) and membrane strips from example 2 having a width of 3.3 cm and a length of 21 cm, 18 strips in total, are wound with coarse PP fabric and transferred to a 500 ml polypropylene screw-cap jar. The sulfation solution which is temperature-controlled to 40° C. is transferred to the screw-cap jar. The screw-cap jar is tightly sealed.

The reaction vessel is shaken at 40° C. for 20 hours. The membrane filter strips are then rinsed and impregnated as follows:

10 min running reverse osmosis water,
10 min shaking with 1000 ml of 1M NaCl,
10 min running reverse osmosis water,
10 min in a solution of 30% by weight glycerol and 70% by weight water.

These are then dried at 80° C. for at least 12 hours.

Example 4: Permeability Determination of Microfilter Membranes 47 mm discs are punched out from sulfated cellulose microfilter membranes according to example 3. These are wetted with reverse osmosis water and rinsed for 5 min under running reverse osmosis water. A punched blank is incorporated in a Sartorius Type 16249 pressure filter holder. The measurement is carried out at 20 to 25° C. and 0.1 bar positive pressure. The time taken for 100 g of medium to flow through the membrane filter is measured. The unit of flow thus determined is stated as ml/(cm$^2$·min·bar). Both reverse osmosis water and 10 mM potassium phosphate buffer with pH 7 are used as media.

The discs may be used for further investigations after determination of the flow.

Example 5: Quantitative Determination of the Degree of Sulfation by Titration 30 mm discs are punched out from the sulfated cellulose microfilter membranes using a round punch. A 30 mm punched blank is incorporated in a dead-volume optimized filter holder. The active filter surface is 5.7 cm². The filter holder is filled with reverse osmosis water with exclusion of air bubbles. The filter holder is connected to a multichannel cartridge pump from Watson Marlow (Type 205 U), of which the lines are free of air bubbles. The cartridge pump output is circa 5 ml per minute. The following media are then pumped in series through the membrane filters, each for a 4 min period: 1M NaCl, 1M HCl, 1 mM HCl, reverse osmosis water.

A 40 ml glass beaker with magnetic stirrer bars is then placed under the output side of the filter holder. 1M NaCl is then supplied for a further 4 min. The eluate collected is then titrated by means of potentiometirc indication. The titrant is 5.0 mM aqueous sodium hydroxide solution. To this end, the consumption of a 5 mM aqueous sodium hydroxide solution is determined up to the equivalence point at pH 7.0. The quantitative amount of aqueous sodium hydroxide solution consumed is directly proportional to the quantitative amount of sulfate groups on the membrane. From the active surface of the membrane available and the consumption of aqueous sodium hydroxide solution and also the mass of cellulose per cm², the degree of sulfation, which is the proportion by mass of sulfate groups on the sulfated cellulose, can be calculated.

Formula:
Sulfate Group Density:

$$n_{sulfate} (\mu mol/cm^2) = c(NaOH) \times t(NaOH) \times V(NaOH) \times 1000/A$$

where
c(NaOH) quantitative concentration of aqueous sodium hydroxide titrant in mol/l
V(NaOH) volume in ml of titrant consumed at the equivalence point (pH 7)
t(NaOH) correction factor of titrant
1000 conversion factor from mol/l to µmol/ml
A active filter surface in cm²
and where
M(SO₃) molar mass of SO₃ in µg/µmol.

Formula:

$$\text{Degree of sulfation in \% by weight} = (n_{sulfate} \times M(SO_3))/(m_{cellulose}(n_{sulfate} \times M(SO_3))) \times 100\%$$

where
$m_{cellulose}$ mass of cellulose in µg per cm² of punched blank.

The results of the degree of sulfation of samples 1 to 5 are summarized in Table 2.

Example 6: Determination of the Binding Capacity for Lysozyme

Membrane samples each having an active membrane surface of 17.6 cm² are shaken three times for 5 minutes in 35 ml of 10 mM potassium phosphate buffer (KPi), pH 7.0, at about 80 revolutions per minute (rpm) and then placed in 35 ml of a solution of 2 mg/ml lysozyme in 10 mM Kpi, pH 7.6, at 20 to 25° C. for 12 to 18 hours. The membrane samples are then rinsed for 2×15 minutes in 35 ml of 10 mM KPi buffer (pH 7.0) each time. The membrane samples are then shaken in 20 ml of 10 mM KPi buffer (pH 7.0) and in 1M aqueous NaCl solution. The amount of protein eluted is determined by measuring the optical density (OD) at 280 nm.

The results of the binding capacity for lysozyme for samples 1 to 5 and Sartobind® S are summarized in Table 2.

Example 7: Binding of Host Cell Proteins (HCP)

To determine the binding of host cell proteins, a 10-fold concentrated HCP solution in PBS buffer (phosphate-buffered saline solution, pH 7.4) is used without antibody, prepared, in the case of a contract producer, in a "mock" run (culturing of a cell line without antibody production) of a Chinese hamster ovarian cell line. The HCP solution is diluted 1:10 in 20 mM TRIS/HCl buffer (pH 7.4) and the conductivity is adjusted to 10 mS/cm by the addition of NaCl. 1000 ml of the diluted HCP solution are used to load the membranes. The HCP concentration is determined by means of ELISA ("enzyme-linked immunosorbent assay ELISA Cygnus CM015") according to the procedure specification. The concentration of host cell proteins (HCP) is 7 µg/ml.

3 membrane layers (sample 4) are fixed in a membrane holder. The membrane stack in the membrane holder has a membrane surface of 15 cm², an in-flow surface of 5 cm² and a bed height (thickness of the membrane stack) of 750 µm. The membranes in the membrane holder are flushed with 20 mM TRIS/HCl buffer (pH 7.4) to displace the air and then connected to an "Äkta® Explorer 100" chromatography system from GE Healthcare.

The membranes or the membrane stack are then investigated with respect to the HCP binding using a test program comprising four steps. The four steps of the test program are specified below:

1. Equilibrating the membrane with 10 ml of 20 mM TRIS/HCl buffer (pH 7.4) having a conductivity of 10 mS/cm,
2. Loading of the membrane with 100 ml of HCP solution,
3. Washing with 10 ml of 20 mM TRIS/HCl (pH 7.4, conductivity 10 mS/cm) and
4. Eluting with 10 ml of 1M NaCl in 20 mM TRIS/HCl buffer (pH 7.4).

All steps are carried out at a flow rate of 10 ml/min. In all steps, the absorption is measured in the detector at 280 nm following on from the membrane unit. The breakthrough curves are shown in FIG. 3.

Example 8: Determination of the Binding Capacity for Small, Inactivated Influenza Viruses Influenza A Puerto Rico/8/34, H1N1 is produced in adhering MDCK cells (GMEM medium) (cf. Y. Genzel et al., Vaccine 22 (2004), 2202-2208). After culturing, the culture broth is filtered via two filtration steps in succession (pore size 5 µm and 0.65 µm filter depth, GE Water & Process Technologies) and is subsequently chemically inactivated with 3 mM β-propiolactone at 37° C. for 24 hours. After inactivation, the solution is again clarified (0.45 µm membrane filter, GE Water & Process Technologies) and subsequently concentrated 20-fold via cross flow filtration (750 kDa MWCO, GE Healthcare) (cf. B. Kalbfuss et al., Biotechnol. Bioeng. 97 (1), 2007, 73-85). The concentrated samples are stored at −80° C. until required for use.

The frozen virus aliquots (3×2 ml) are thawed in a water bath, mixed and centrifuged at 9000 g for 10 min. The supernatant is subsequently diluted 1:3 with the binding buffer (10 mM Tris, pH 7.4 and 50 mM NaCl).

The solution thus prepared is used for the determination of the dynamic binding capacity. All experiments were carried out on an "Äkta® Explorer 100" chromatography system from GE Healthcare. The units tested for the experiments consist of 15 membrane layers with an in-flow surface of 0.36 cm$^2$ and a bed volume of 0.14 ml. The equilibration is carried out with 10 mM Tris, 50 mM NaCl pH 7.4. After equilibration, 26 ml of the virus solution is loaded onto the unit and 2 ml fractions are collected continuously. The flow rate during loading is 1 ml/min. The hemagglutinin (HA) activity is quantified in the various fractions. After loading, the membrane units are rinsed with equilibration buffer until the baseline is reached and are subsequently eluted with 10 mM Tris, 2.0 M NaCl pH 7.4. The eulate and the rinse fractions are also collected and their HA activity also analyzed.

The virus concentration is determined in the continuous flow fractions and are quantified via the hemagglutination assay (cf. B. Kalbfuss et al., Biologicals 36 (2008), 145-161). The binding capacity for influenza viruses is measured for all samples and the capacity is calculated at 10%, 25% and 50% breakthrough, i.e. the amount of viruses bound per volume of separation material are attained up to 10% or 25% or 50% of the virus concentration of the starting solution. The dynamic binding capacity was calculated as follows:

$C_0$: virus concentration in the starting solution (virus particles/ml=part./ml)
$V_x$: loading volumes which were reached up to x % breakthrough (ml)
$A_x$: number of virus particles in the continuous flow which were reached up to x % breakthrough
$V_B$: bed volumes of the unit tested Dynamic binding capacity up to $x$ % breakthrough
(part/ml)=$(V_x \times C_0 - A_x)/V_B$ The results of the binding capacities of samples 1 to 5 and for Sartobind® S are summarized in Table 2.

outer main surfaces for adsorptive substance separation wherein the degree of sulfation of the cellulose hydrate matrix is more than 20% by weight.

2. The sulfated cellulose hydrate membrane a claimed in claim 1, wherein the mean pore size of the membrane is between 0.5 and 5.0 μm.

3. The sulfated cellulose hydrate membrane as claimed in claim 1, wherein the degree of crosslinking of the cellulose hydrate matrix is 0.05 to 0.5.

4. A method for preparing a sulfated cellulose hydrate membrane as claimed in claim 1, comprising the steps of:
   providing a cellulose membrane with a pore size of 0.1 to 20 μm;
   crosslinking the cellulose hydrate matrix using a crosslinker having at least two functional groups in the molecule which react with the hydroxyl groups of the cellulose hydrate matrix; and
   sulfating the crosslinked cellulose hydrate matrix.

5. The method as claimed in claim 4, wherein the crosslinker is selected from the group consisting of diepoxide compounds, diisocyanates, epichlorohydrin, epibromohydrin, dimethylurea, dimethylethyleneurea, dimethylchlorsilan, bis (2-hydroxyethylsulfone), divinylsulfone, alkylene dihalides, hydroxyalkylene dihalides and diglycidyl ethers or a mixture thereof.

6. The method as claimed in claim 4, wherein 1, 4-butanediol diglycidyl ether or ethylene glycol diglycidyl ether is used as crosslinker.

7. The method as claimed in claim 4, wherein the concentration of the crosslinker in the crosslinking solution of 10 to 30% by weights.

8. The method as claimed in claim 4, wherein the sulfation is effected by reacting the crosslinked cellulose hydrate matrix having a Lewis base-SO$_3$ complex.

9. The method as claimed in claim 4, wherein the sulfation is effected by reaction with a SO$_3$-pyridine complex.

10. The method as claimed in claim 9, wherein the concentration of SO$_3$-pyridine-complex in the sulfation solution is 1 to 40% by weight.

TABLE 2

Results summary

| | Sample | | | | | |
|---|---|---|---|---|---|---|
| | 1 | 2 | 3 | 4 | 5 | Sartobind ® S |
| Pore size of cellulose starting membrane (μm) | 3 | 3 | 3 | 3 | 1.2 | |
| Crosslinking according to | none | Example 1 | none | Example 1 | Example 1 | Not applicable |
| Sulfation method according to | Example 3 | Example 3 | Example 2 | Example 2 | Example 2 | Not applicable |
| Degree of sulfation in % by weight | 0.64 | 19.37 | 1.26 | 10.34 | 16.65 | — |
| Binding capacity with influenza part./ml | | | | | | |
| Up to 10% breakthrough | 0.0 | $5.0 \cdot 10^{11}$ | 0.0 | $3.4 \cdot 10^{12}$ | $6.4 \cdot 10^{12}$ | $4.9 \cdot 10^{11}$ |
| Up to 25% breakthrough | $4.3 \cdot 10^{11}$ | $3.1 \cdot 10^{12}$ | $4.0 \cdot 10^{11}$ | $4.3 \cdot 10^{12}$ | Not reached* | $4.9 \cdot 10^{11}$ |
| Up to 50% breakthrough | $4.3 \cdot 10^{11}$ | $4.4 \cdot 10^{12}$ | $4.0 \cdot 10^{11}$ | $5.7 \cdot 10^{12}$ | Not reached* | $2.3 \cdot 10^{12}$ |
| Binding capacity with lysozyme (mg/mL) | 32.6 | 7.0 | 30.0 | 4.8 | 8.1 | 37.0 |

*In sample 5, owing to the very high binding capacity of this membrane for influenza viruses, no 25% or 50% breakthrough were able to be reached with the loading volume of 26 ml of virus solution mentioned in Example 8.

The invention claimed is:

1. A sulfated cellulose hydrate membrane which is a sheetlike adsorption membrane defining two outer main surfaces, the sulfated cellulose hydrate membrane comprising a crosslinked cellulose hydrate matrix with pores which extend from one outer main surface to an opposing outer main surface of the membrane, wherein the cellulose hydrate membrane has sulfate ligands on its inner surfaces and on its 11. The method as claimed in claim 4, wherein the sulfation is effected at a temperature of 20 to 90° C.

12. A method of purifying viruses or virus fragments comprising:
   preparing a sulfated cellulose hydrate membrane as claimed in claim 1; and
   contacting the membrane with a solution containing the viruses or virus fragments.

13. The method of claim 12 wherein the viruses have a molecular mass of greater than $10^7$ Da.

14. The method of claim 12 wherein the viruses are influenza viruses.

* * * * *